(12) United States Patent
Chakrabarty (10) Patent No.: US 7,998,676 B2
(45) Date of Patent: Aug. 16, 2011

(54) METHODS AND APPARATUSES FOR SORTING OBJECTS IN FORENSIC DNA ANALYSIS AND MEDICAL DIAGNOSTICS

(75) Inventor: Tania Chakrabarty, Chicago, IL (US)

(73) Assignee: Arryx, Inc., Chicago, IL (US)

( * ) Notice: Subject to any disclaimer, the term of this patent is extended or adjusted under 35 U.S.C. 154(b) by 48 days.

(21) Appl. No.: 12/232,165

(22) Filed: Sep. 11, 2008

(65) Prior Publication Data

US 2009/0075826 A1 Mar. 19, 2009

Related U.S. Application Data

(60) Provisional application No. 60/960,059, filed on Sep. 13, 2007.

(51) Int. Cl.
*C12Q 1/68* (2006.01)

(52) U.S. Cl. ........................................... 435/6

(58) Field of Classification Search ........................ None
See application file for complete search history.

(56) References Cited

U.S. PATENT DOCUMENTS

| | | | |
|---|---|---|---|
| 5,436,157 A | 7/1995 | Herr et al. | |
| 5,629,147 A | 5/1997 | Asgari et al. | |
| 6,540,895 B1 * | 4/2003 | Spence et al. | 204/450 |
| 6,863,406 B2 * | 3/2005 | Grier et al. | 359/614 |
| 7,402,131 B2 | 7/2008 | Mueth et al. | |
| 2002/0182751 A1 | 12/2002 | Herr et al. | |
| 2005/0130173 A1 | 6/2005 | Leamon et al. | |
| 2005/0244879 A1 | 11/2005 | Schumm et al. | |
| 2005/0255606 A1 | 11/2005 | Ahmed et al. | |
| 2006/0008823 A1 | 1/2006 | Kemp et al. | |
| 2006/0134603 A1 * | 6/2006 | Plewa et al. | 435/4 |
| 2006/0228758 A1 | 10/2006 | Muchhal et al. | |
| 2007/0029257 A1 | 2/2007 | Mueth et al. | |
| 2007/0077570 A1 * | 4/2007 | Lao et al. | 435/6 |

* cited by examiner

*Primary Examiner* — Christopher M. Babic
(74) *Attorney, Agent, or Firm* — Jean C. Edwards, Esq.; Edwards Neils PLLC (57) ABSTRACT

The present invention relates to an apparatus and method of sorting objects and identifying the objects in a forensics sample, including using holographic optical trapping to sort objects from contaminants, and performing (single cell) PCR-based STR analysis on the objects to determine their identification. In addition, the chip used as a support for sorting the objects can also be used for performing single cell PCR-based STR analysis. In another embodiment, a microfluidics chip is used to stream the sample and sort the objects, before single cell PCR-based STR analysis is performed. The chip used for sorting utilizing HOT in the absence or presence of microfluidic streaming and sorting can also be the same as that used for the single cell PCR-based STR analysis.

27 Claims, 6 Drawing Sheets

METHODS AND APPARATUSES FOR SORTING OBJECTS IN FORENSIC DNA ANALYSIS AND MEDICAL DIAGNOSTICS

The present application claims priority from U.S. Provisional Patent Application No. 60/960,059, filed Sep. 13, 2007, the contents of which are herein incorporated by reference in their entirety.

BACKGROUND OF THE INVENTION

1. Field of the Invention

The present invention relates to methods and apparatuses for sorting objects in forensic DNA analysis and medical diagnostics. More particularly, the present invention relates to the sorting of sperm for a single cell polymerase chain reaction (PCR) method which is used in forensic DNA analysis, such as STR analysis, to identify persons/assailants in sexual assault cases. Further, the present invention relates to the use of on-chip PCR in forensic DNA analysis. Finally, the present invention of sorting cells and single cell PCR has applicability outside of forensics, such as in the field of cancer diagnostics, where STR-based cell identification is becoming popular to distinguish cancer cells from healthy cells.

2. Description of the Related Art

Conventional forensic DNA specimens are commonly matched to alleged criminal suspects in modern law enforcement using human identification systems involving the amplification of highly polymorphic short tandem repeats (STRs) by polymerase chain reaction (PCR). PCR is a powerful tool which allows for replicating/amplifying trace amounts of DNA fragments into quantities that can be analyzed in a meaningful way. This technology has been adapted for DNA sequencing, DNA fingerprinting etc., and has the ability to detect specific DNA fragments in samples.

Thus, forensic DNA analysis is accomplished using the high power of discrimination and rapid analysis speed of STR markers in the human genome, and has now become the most popular method of choice in forensic DNA analysis.

By way of explanation, STRs are short stretches of DNA that arise when a pattern of two to six nucleotides are repeated and the repeated sequences are adjacent to each other. STR sequences vary in length of the repeat unit, number of repeats and in the rigor with which they conform to an incremental repeat pattern. STR markers are scattered throughout the genome and occur as frequently as one every 10,000 nucleotides. Based on 2001 International Human Genome Sequencing Consortium data, STRs or microsatellites account for approximately 3% of the total human genome. Currently 13 STRs are analyzed for human identification in forensic analysis, using well-known PCR methods.

Although STR analysis is commonly used, it suffers from several pitfalls, the most significant of which arises from contamination of the query DNA samples prior to STR analysis via PCR methods, and the time it takes to perform the PCR analysis.

For example, the DNA to be analyzed for STRs from sexual assault evidence should ideally come from the sperm of the assailant. However, the sperm sample is often commonly contaminated with (1) epithelial cells lining the vagina, and occasionally, with (2) epithelial cells from the mouth (buccal cells), and (3) cells from the skin, as well as cells in the urine sample. One might also expect to see erythrocytes, neutrophils, foam cells (non-descript epithelial cells), etc., in sexual assault crime scene samples as well.

Thus, it is clear that better and more accurate STR analysis will be achieved if the sperm cells could be separated from any or all of the contaminating cells before PCR is performed.

Commonly used methods like differential extraction cannot completely separate male (assailant) sperm and female (victim) epithelial cell DNA. For example, initial lysis using reductant free solution, lyses epithelial cells (the most common contaminant in a sexual assault forensic sample) and leaves sperm cells intact for effective separation of DNA fractions. However, differential lysis often causes immature sperm cell lysing. Therefore unwanted DNA often gets coamplified during PCR. This leads to mixed profile and incomplete STR analysis causing more than 50% of STR analysis based human identification to fail.

In addition, another limitation in solving forensic cases comes from the limited availability of cells for analysis. This may be due to limited evidence samples being present, degradation of the DNA and cell samples in general over time, and/or the presence of very few sperm cells in a sexual assault crime sample, to be able to solve the case based on standard PCR.

Thus, a method that would prevent or alleviate the above problems, and provide a fast, effective, and reliable method of sorting cells with single cell precision in a forensics sample, is desired.

SUMMARY OF THE INVENTION

The present invention relates generally to sorting objects, primarily, at the single cell level, for use in forensics DNA analysis and in medical diagnostics. More specifically, the present invention relates to a method of sorting and identifying objects in a forensics sample, and includes providing a holographic optical trapping apparatus for sorting of objects in a forensics sample, the sample which contains objects (wanted and unwanted) to be separated; providing a sample chip (microfluidics-based or otherwise) containing chambers for separation of the objects; optically trapping the objects in the forensics sample and sorting them using optical trapping into the wanted and unwanted objects; removing at least one wanted object from the sample using HOT or microfluidics or both; and performing PCR-based STR analysis on the wanted object to determine their identification.

In one embodiment consistent with the present invention, the wanted objects are cells, in particular sperm, and the unwanted objects are contaminants such as epithelial cells, non-sperm objects, etc.

In one embodiment consistent with the present invention, prior to the optical trapping step, the method further includes providing the forensics sample in a fluidic stream in a microfluidics chamber; and streaming the sample through the microfluidics chamber. The wanted objects may be sorted into individual chambers, where single cell PCR-based STR analysis can be performed.

In one embodiment consistent with the present invention, the microfluidics chamber includes an input chamber which contains the forensic sample, and the sample is streamed into at least one output chamber, where single cell PCR-based STR analysis can be performed.

In one embodiment consistent with the present invention, a method of identifying the objects in a forensics sample and separating them includes providing a microfluidics chamber having an input chamber and at least one output chamber; providing a forensics sample in the input chamber, the sample containing objects to be separated; separating the objects using a microfluidics stream in the microfluidics chamber, into wanted and unwanted objects; removing at least one wanted object from the sample into at least one output chamber; and performing PCR-based STR analysis on the wanted object to determine an identification of the wanted object.

The performing step of each of the above main embodiments, may be performed on a single chip, and/or single cell PCR-based STR analysis is performed in the output chamber.

In one embodiment consistent with the present invention, an apparatus for sorting objects includes a holographic optical trapping apparatus containing a support on which a sample is disposed, the optical trapping apparatus which optically traps and sorts wanted objects from unwanted objects in the sample; and an apparatus for performing PCR-based STR analysis on the wanted objects.

In one embodiment consistent with the present invention, the wanted objects are cells—particularly sperm—and/or single cell PCR-based STR analysis is performed, and/or is performed on a single chip.

In one embodiment consistent with the present invention, the apparatus further includes a microfluidics chip for streaming the sample prior to optical trapping of the wanted objects.

In one embodiment consistent with the present invention, an apparatus for sorting objects includes a microfluidics chip containing an input chamber and at least one output chamber, the input chamber containing a sample; wherein the microfluidics chip streams the sample such that the wanted objects are sorted from the unwanted objects in the sample and the wanted objects are sorted into at least one output chamber; and an apparatus for performing PCR-based STR analysis on the wanted objects.

In another embodiment consistent with the present invention, the apparatus further includes a holographic optical trapping apparatus for sorting the wanted objects from the unwanted objects in the sample, from the input chamber into the at least one output chamber.

In another embodiment consistent with the present invention, the wanted objects are cells—particularly sperm—and the unwanted objects are contaminants, and a single chip is used to sort the objects and perform the PCR-based STR analysis, and/or the PCR-based STR analysis is single cell PCR-based STR analysis.

With the present invention, single cell PCR-based STR analysis will resolve sexual assault cases where multiple assailants are involved, and will provide an opportunity for solving cases where limited material (i.e., a limited number of eluted sperm) is available for bulk (multi-cell PCR-based) forensic analysis to be feasible and reliable. Further, single cell PCR-based STR analysis will resolve the issues of contamination (i.e., where epithelial cells of the victim are mixed with the sperm of the assailant, which causes the DNA of the victim to be co-amplified with the DNA of the assailant). Thus, single cell PCR will solve the primary cause of STR analysis failure for human identification by ruling out co-amplification.

The ability to work with few cells (i.e., perform single cell PCR) is important in identifying the assailant in a forensic case which otherwise cannot be solved, and it also enhances the chance of ruling out involvement of incriminated persons where limited samples are available (i.e., azospermic males).

Further, single cell PCR improves the speed of processing the sample, since sorting single cell, or rather a few single cells (for statistical purposes), takes less time than when dealing with hundreds of cells (as is ordinarily required).

The use of HOT for single cell sorting prior to PCR, lends the present invention to the use of disposable chips, which provide a completely sterile environment for sample handling. This will avoid contamination issues (i.e., from a user/technician handling the sample) on a single or multi-platform.

Thus, one can preserve evidence data in a sterile environment for future re-analysis if needed.

Further, by using microfluidic chips, the sample volume to be handled in the present sorting and identification process, will be largely minimized. The present invention will also be inexpensive to operate, since smaller volumes of samples imply less reagents are required overall. The present invention is flexible enough to offer different choices for cell sorting (i.e., using HOT alone or using microfluidics alone, or combining both), different modes of cell lysis and DNA extraction (on-chip or in separate tubes), and different modes of PCR (on-chip using a flatbed thermocycler, or in microcentrifuge tubes using conventional PCR machines).

Further, with the present invention, both HOT and microfluidics-based cell sorting are gentle processes and do not cause immature cell lysing.

The present invention does not require sample staining prior to sample processing (unlike LCM (laser capture microdissection) which has the capability for single cell extraction)—thereby cutting down on the cost of dyes and additional sample processing steps. However, the proposed invention is compatible with fluorescently stained samples, if needed.

Since embodiments of the present invention include a visualization-based technique (i.e., microscopic visualization, or even machine vision in the event of a completely automated machine), the present invention offers better documentation for forensic sample processing, such as recording all the intermediate steps, and recording the number of cells being analyzed in a given case or documenting the morphology of the cells analyzed.

The present invention is amenable to complete automation, whereas conventional techniques, such as differential extraction, is not. Further, the apparatus can be miniaturized and made portable and sample chips to carry out sorting, and PCR can be made disposable.

Although the present invention described herein for use in forensic DNA analysis primarily relates to sexual assault cases and focuses on sperm separation, the general method of single cell PCR based STR analysis is extendable to other types of forensic samples where separation of a significant number of a certain cell type for human identification, may be a challenge. Since differential extraction relies entirely on a chemical process with no microscopic visualization, a technique such as that of the present invention, that can visualize and extract the cell(s) of interest for STR analysis would be of great benefit to the field of forensics.

The present invention extends the scope of single or few cell based forensic DNA analysis beyond sexual assault crime cases to human identification of war victims or soldiers (in the realm of military forensics, for example). It could also be used for paternity testing where, often, collection of enough sample(s) from the suspect is a problem.

Further, the present invention may be used in areas of cancer diagnostics where PCR-based STR analysis is often used to distinguish cancerous cells from normal cells in a specimen sample and STR analysis at single cell level will provide additional information about the severity and progression of the disease by accounting for the percentage of cells in the specimen sample that looks healthy versus cancerous.

There has thus, been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the concepts upon which this disclosure is based may readily be utilized as a basis for the designing of other structures, methods and systems for carrying out the different purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to methods and apparatuses for sorting objects in forensic DNA analysis. In particular, the present invention uses a novel approach—namely, single cell PCR-based STR analysis, with (or without) holographic optical trapping (HOT), and/or microfluidic chambers, to separate sperm from contaminants and perform identification of assailants in forensics DNA analysis. The chip used for the purpose of sorting the objects can also be used to perform the downstream steps of cell lysis, DNA extraction and PCR (on-chip PCR).

Further, a microfluidics chip is used to stream the samples and sort the objects (cells) of interest from unwanted contaminants before performing single cell based PCR analysis. Rather than using HOT alone for sorting, the procedure uses microfluidics based sorting prior to using HOT in the case of samples where a larger number and variety of contaminants are present. Such a combination of HOT with microfluidics for sorting may also improve throughput (cut down sorting time prior to PCR) and purity when compared to using HOT alone for sorting. The chip used for object identification and sorting can be the same as the chip meant for single cell PCR for STR analysis.

Single cell PCR for forensics has several advantages including the ability to avoid contamination from unwanted cells, the ability to handle limited evidentiary samples, ability to detect multiple assailants, improved speed and automation, as well as likely reduction in costs. On-chip PCR for forensic analysis also has multiple advantages such as portability, miniaturization, and maintaining a sterile environment for handling.

The present invention proposes a novel use of on-chip PCR for forensic analysis, thereby creating a new kind of disposable chip which would minimize intermediate handling. The proposed invention includes a visualization-based method and offers the ability to document all the intermediate processing steps in analyzing a sample.

While the present invention describes details in the light of forensics, the scope goes beyond forensics, such as into the field of cancer diagnostics, where identifying rare cells (i.e., cancerous cells), and distinguishing them from normal ones based on STR, is of great value.

In a first embodiment consistent with the present invention, holographic optical trapping (HOT) is used for identifying and trapping sperm cells, and sorting them from other contaminating cells in a sexual assault crime sample.

The HOT apparatus 100 (see U.S. Pat. No. 6,055,106, to Grier et al., for example, which is herein incorporated by reference), includes a laser 101 which is used as a light source, to optically trap and manipulate objects in a sample 102 on a support 103 (see FIG. 1). Specifically, the laser 101 emits a collimated laser beam 104 which is shaped by a diffractive optical element (DOE) 105, such as a spatial light modulator (SLM) 105, and transferred to a back aperture of an objective lens 106 via, for example, telescope lenses 107, 108 and dichroic mirror 109. The beam 104 is diffracted by the DOE 105 into a plurality of beamlets and forms a plurality of independently movable optical traps 110 on the support 103 of a microscope apparatus (of which objective lens 106 is a part). The support 103 and sample 102 are illuminated by the beam 111 emitted from a light source 112. The point B' is conjugate to B in FIG. 1. Note, however, that telescope lenses 107, 108 may be eliminated from the apparatus 100 and replaced with a single transfer lens, if desired.

Figure 1:
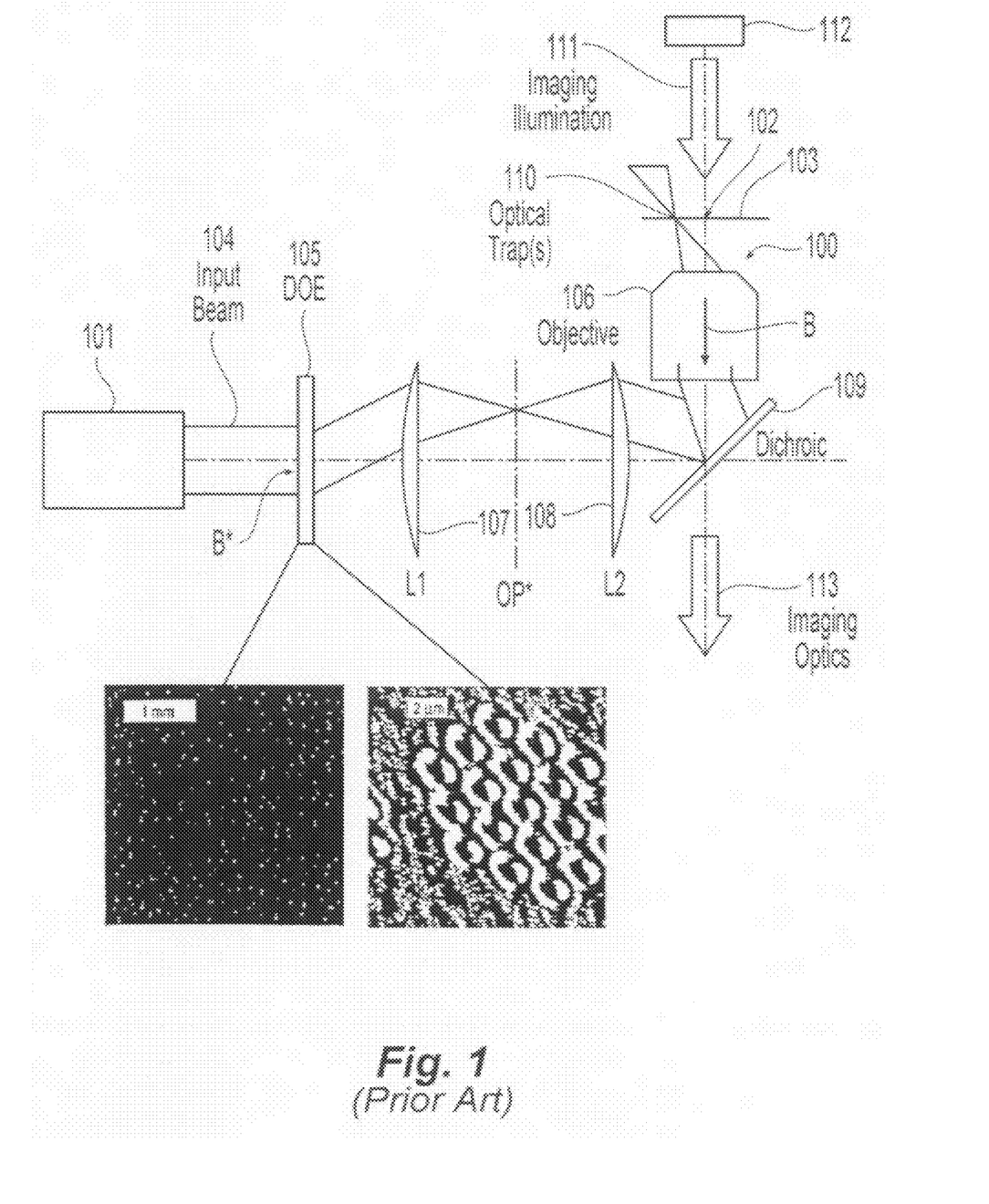
FIG. 1 is a schematic of a holographic optical trapping apparatus according to one embodiment consistent with the present invention.

Imaging optics 113, such as a CCD camera, etc., are used to view the optically trapped objects in the sample 102. The apparatus 100 may be connected to a computer (not shown) which can control the optical trapping and can record the data during operation.

In this embodiment, the holographic optical trapping apparatus is used to sort objects in a forensics sample 102. The sample 102 of sperm and other cells, is obtained from the crime scene, and the cells in the sample 102 are eluted and placed on a microfluidic chip 200 (see FIG. 2) for example, by pipetting, gravity, or by other active or passive mechanisms. The microfluidic chip 200 is placed on a microscope platform 103 for visual inspection—either manual or automated using computer control.

Figure 2:
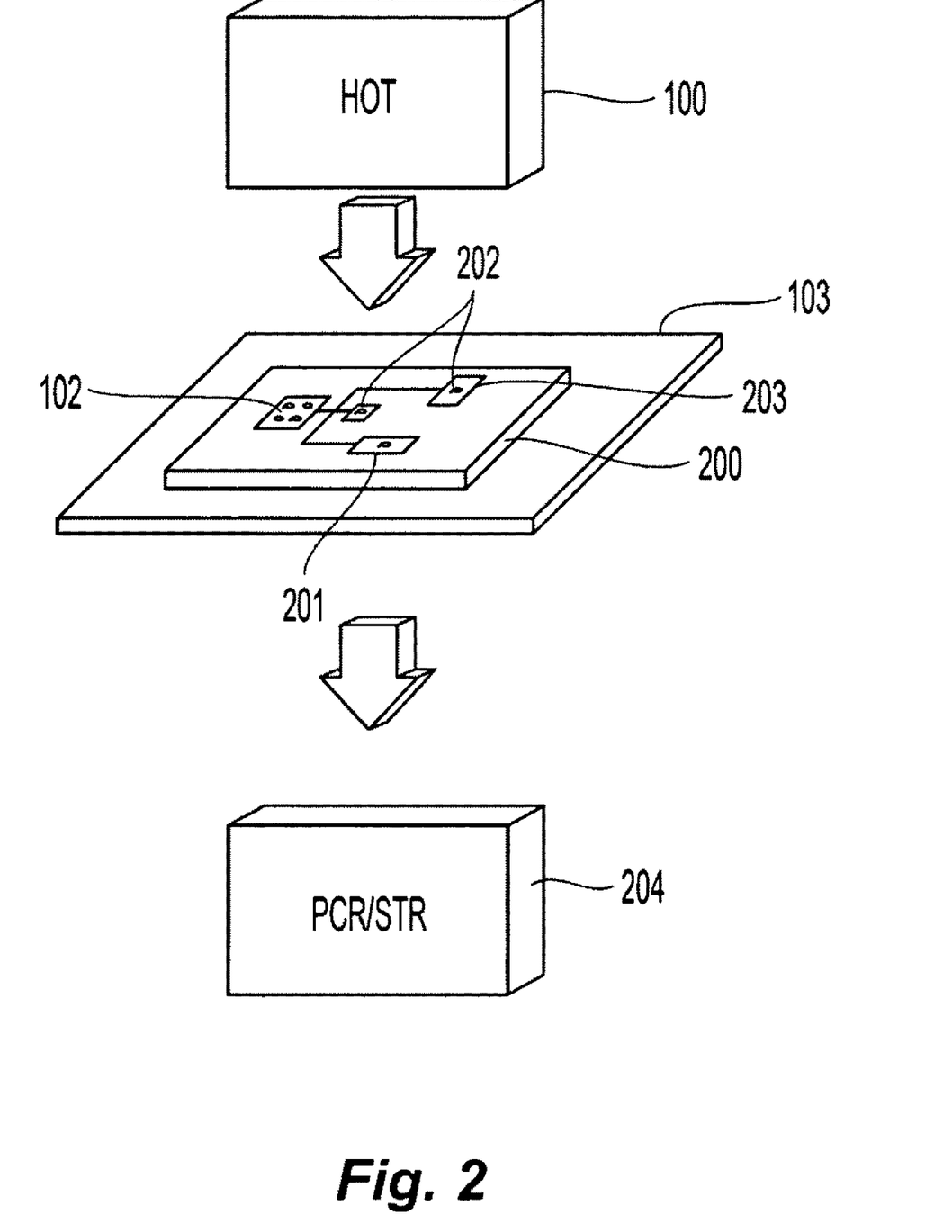
FIG. 2 is a schematic of an object sorting apparatus according to one embodiment consistent with the present invention, including a microfluidics chip, a holographic optical trapping apparatus, and an apparatus which performs PCR-based STR analysis.

Thus, HOT 100 is used to separate the sperm cells in the forensics sample 102, by visual (microscope or monitor) inspection, from other contaminating cells, by moving the optically trapped sperm from one area of the microfluidic chip 200 into individual chambers 201-203 on the same chip 200, for example.

Then, PCR-based STR analysis 204 is performed to identify the person (typically matching the STR signatures stored in the CODIS database) whose DNA signature matches with the STR analysis of the sperm (specimen sample). The PCR-based STR analysis is in itself well-known in the art and has been broadly commercialized.

In particular, the chip 200 is placed on a flatbed thermocycler, where the extracted DNA is amplified by PCR using STR primers which are commercially available for forensic cases. Alternatively, a custom-designed appropriate primer can be used where forensic cases are not involved. The number of thermocycles is increased to leave enough DNA from the individual cells at the end of the PCR cycling.

DNA extraction may be performed by centrifugation (post cell lysis) or by attaching to magnetic beads, where the DNA is eluted from the beads (magnetic or others), by changing the pH (altering the charge on the DNA, i.e., by affecting binding of the DNA to the beads) or by changing the salt concentration of the elution buffer.

Once PCR is completed, the amplified DNA is run on gels (typically) for STR analysis on the amplified DNA that has undergone PCR, where each PCR reaction corresponds to amplified DNA from a single sperm. Commercially available instruments may be used for this purpose.

Conventionally, a significant number of cells were required to get a reliable STR readout signal. However, with the gentle method of HOT-based sperm separation and improved sensitivity, a more reliable separation of sperm from contaminating non-sperm cells can be performed, and one can scale down the sample collection in terms of number of sperm cells needed for PCR-based STR analysis from about 200 (as is required in conventional methods), to a few cells, or even to the level of single cell PCR—greatly increasing its efficiency (see chambers 201-203).

Thus, single-cell PCR can be carried out on each individual sperm in chambers 201-203, using standard PCR methods (lysing the sperm one at a time, extracting the DNA).

In another embodiment, the DNA after extraction from single cells, can be transferred to Eppendorf tubes for carrying out PCR reactions prior to STR analysis. Multiple PCR reactions can be carried out at any given time on one machine. However, to avoid DNA loss during transfer from sorting chip to tubes, the PCR may be carried out on-chip using flatbed thermocycles as described above.

Figure 3:
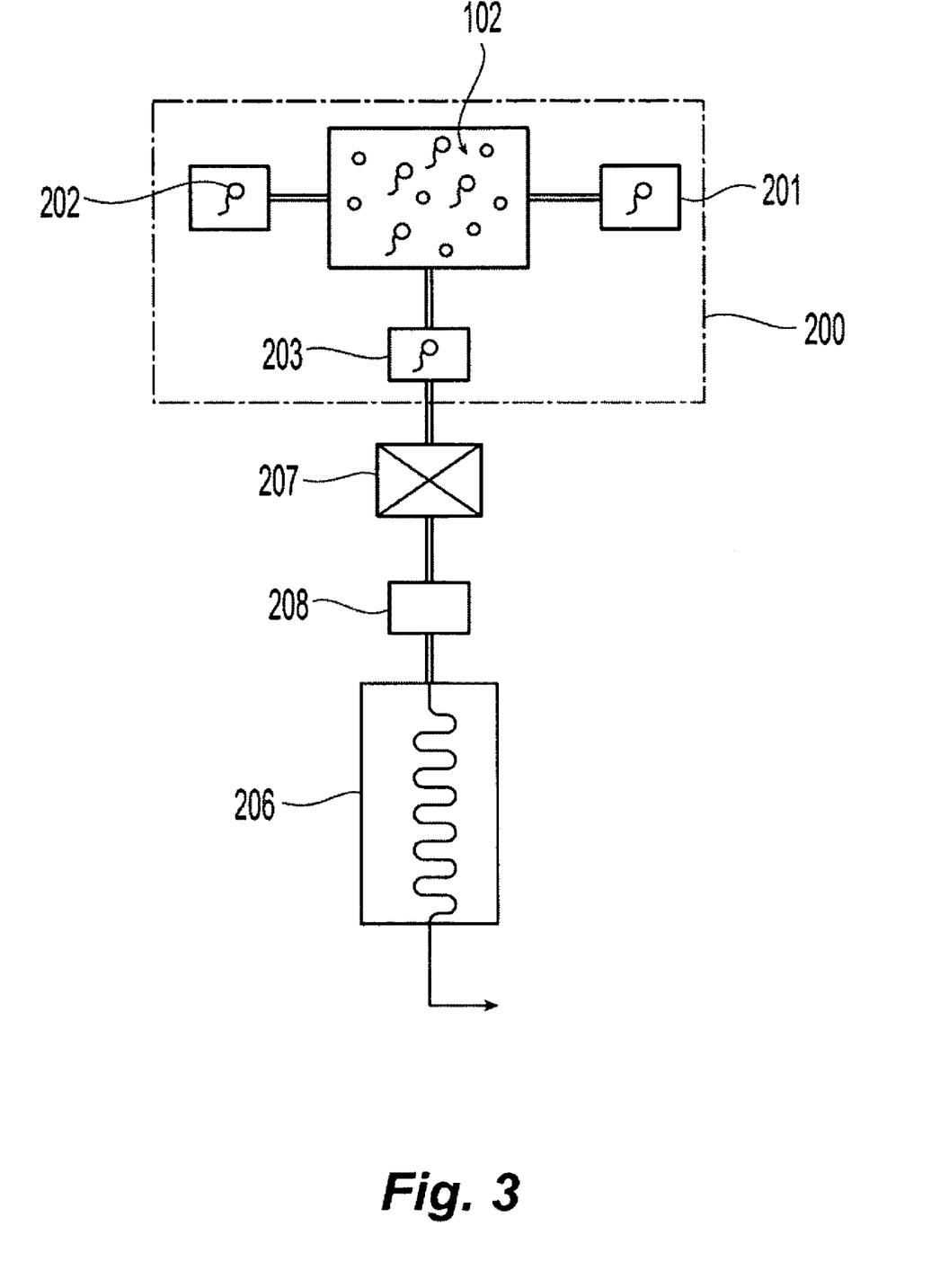
FIG. 3 is a schematic of an object sorting apparatus according to another embodiment consistent with the present invention, including a microfluidics chip, and a single cell PCR/STR apparatus

In addition to standard PCR/STR analysis in tubes or on plates, in one embodiment, the analysis can also be performed on a single chip 206 (on-chip PCR) (see FIG. 3). As shown in FIG. 3, in this embodiment, the sperm in sample 102 can be lysed in situ 200, or the sperm in each well or chamber 201-203 can by lysed and passed through a filter 207 to separate the cell debris from the DNA, and only allow DNA to proceed to the next chamber 208, where PCR (bulk) is run (i.e., on DNA from several sperm). The chamber 208 is connected to an on-chip PCR device 206 with the capability of STR readout.

A final STR report is then generated for each individual sperm analyzed, and statistics generated on the STR readouts from individual sperms. The resulting data is matched with the CODIS database for human identification if it is meant for forensic use, for example.

The virtue of individual sperm (single cell) PCR based STR readout is that, it:

(1) solves the contamination problem in multi-cell situations which is currently the major problem in PCR based STR analysis which arises due to co-amplification of unwanted DNA.

(2) it increases the likelihood of detecting multiple assailants (if involved in a sexual assault case) based on the statistical significance of the STR readout (well-established by standard regulations);

(3) it offers the ability to analyze those crime cases where obtaining 200 sperm cells is a challenge due to the limited availability of sample sperm cells, thus, enhancing the chance of ruling out incriminated persons in a sexual assault case, for example; and (4) It speeds up the total processing time since separating one or a few cells is faster than separating many more cells used in standard PCR based analysis.

Thus, one can envision revolutionizing the nature and scope of STR based forensics offering solutions to more cases where sufficient sample collection posed a problem before. Analysis on one or few cells will cut down on sample collection time as well.

In rare cases, where allele dropout is a problem and an STR profile (based on standard bulk PCR analysis) could not be matched to the CODIS database (the dominant allele masking the other), there is a greater likelihood of matching an STR signature as obtained from single cell PCR to the database with relevant statistical calculations, to arrive at the needed probability.

By analyzing STR on individual sperm cells and repeating the analysis for a number of sperm cells from a given sample on a one-by-one basis, one can now reliably solve sexual assault cases where multiple assailants are involved such as in a gang-rape crime. Thus, no deconvolving is needed in resolving STR profiles of individuals from a cell-mixture set.

Further, single-cell PCR based forensics will offer the ability to perform repeat measurements on multiple single cells from a given specimen and more statistically reliable data can be obtained in solving a crime case.

The present invention is also cheaper to operate in microfluidic chips by reducing the cost of reagent. Further, the use of disposables and the scope for miniaturization of a HOT apparatus will increase its portability.

Thus, it can be seen that HOT-based sperm sorting is more reliable than existing techniques without compromising the amplicon DNA. Further, since HOT 100—which uses light to trap and sort entities of interest from a forensic sample 102—is not damaging towards the DNA obtained from the cell samples 102, this method would speed up data collection (i.e., it will take less time to trap one or a few cells than to trap 200 cells), result in improved speed (by cutting down on sample size for single cell PCR-based forensics), and improved purity (differential optical sorting is better than differential lysis which relies on chemical extraction), and provide scope for automation (which essentially none of the existing techniques for forensic DNA analysis currently allow).

The improved purity and quality control of the sperm cells sorted using HOT 100 will facilitate improved PCR and STR analysis 204, thereby helping to resolve a plethora of unsolved cases where contamination by epithelial or other cells poses a problem by amplifying unwanted amplicons from contaminating cells (often from the victim) in conjunction with the desired amplicon from sperm (from the assailant). Note PCR and STR analysis can be performed on contaminants or unwanted objects (i.e., epithelial cells) as well, in order to cross-check the validity of a filed criminal charge.

Alternate sperm sorting techniques, such as chemical separation approaches like differential extraction, or mechanical separation such as vacuum filtration or trak-etch filtration (which are mechanically driven), do not offer visual (microscope based) inspection in sperm sorting as does HOT 100, and are not as efficient. These methods often result in immature lysis of sperm and are harmful towards the DNA to be analyzed for STR readout.

In addition, none of the afore-mentioned existing methods for cell handling before STR analysis have the ability to perform single cell analysis which is an advantage of the present invention. Optical trapping (HOT) 100 offers the unique ability to visualize and trap sperm cells rather than relying on chemical separation approaches where visualization based sorting is not possible.

Thus, the present invention uses single or oligo cell PCR for forensics, which will help resolve sexual assault cases typically unsolved by standard PCR methods. Further, the present invention will resolve cases where the perpetrator is, for example, an oligospermic male. Such males have very low sperm count in their seminal fluid ejaculate which makes standard PCR based STR methods fail where the source DNA to be amplified comes from differential lysis. Thus, the use of HOT 100 and single cell PCR 204 can provide the identification sought in forensics analysis.

Figure 4:
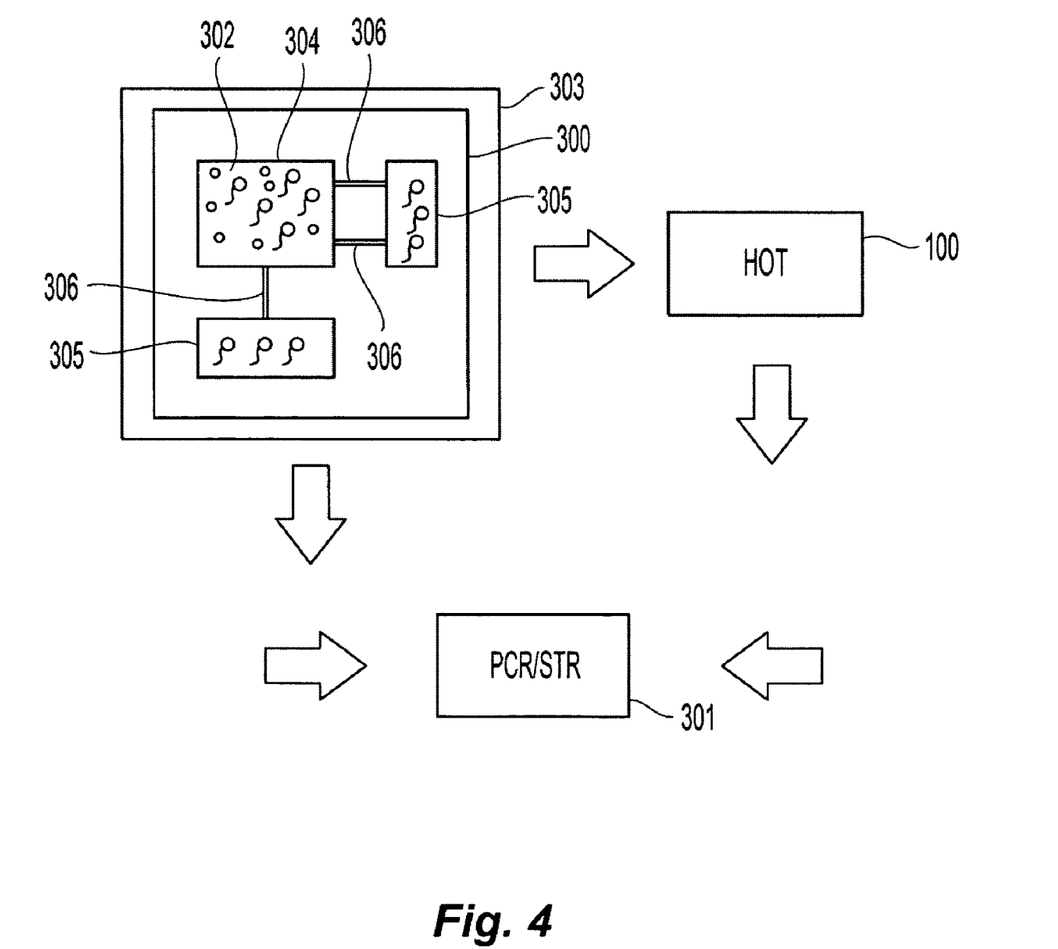
FIG. 4 is a schematic of an object sorting apparatus according to another embodiment consistent with the present invention, including a microfluidics chip, a holographic optical trapping apparatus, and a PCR/STR apparatus.

In a second embodiment consistent with the present invention, a microfluidic chip 300 having chambers can be used with or without HOT 100, to perform the sperm sorting prior to PCR-based STR analysis 301 (see FIG. 4).

In particular, the proposed method of sperm sorting can be performed on an optically clear microfluidic chip 300 thereby allowing operations on very small volume samples. Sample separation using a microfluidic chip 300 with chambers is well-known in the art, and have been broadly commercialized. Here by modulating the idea and incorporating channels at different layers (in depth or z-direction) in the microfluidic chip offers single cell separation.

For example, a custom-made microfluidic chip 300 (see FIG. 4) with an input chamber 304 and multiple output chambers 305 (connected via channels 306 but which can be isolated from one another following sperm sorting), may be used for separating single sperm cells from other contaminants (non-sperm) in the sample 302, as well as from one another. The microfluidic chamber 300 would include a flow injector, and a flow buffer (not shown) through the chamber 304.

In one example, the dimensions of the input chamber 304 are chosen based on the exact sample 302 needs, but for sperm sorting, estimates could be 500 µm length, 100 µm width, and a depth based on the sample volume used, but probably 1-5 µl (or even less, such as in the range of nanoliters since on-chip PCR can be successfully carried out in nanoliter volume). The output chambers 305 may be smaller than the input chamber 304, and of an appropriate size, with the chambers 305 being connected to the input chamber 304 via one channel 306 or multichannels 306, and with one or more chambers 304 connected to the input chamber 305 forming a sterile disposable chip.

The use of a microfluidic chip 300, with or without HOT 100, may be important in reducing reagent cost and maintaining an optimal number density of sperm before doing PCR-based STR analysis in cases where limited starter material is available.

For example, in this embodiment, a swab is obtained from the crime scene, and the sample cells (sperm and contaminants) 302 eluted and placed on a microfluidic chip 300 via active mechanism or pipetting. The microfluidic chip 300 is placed on a microscope platform 303 for visual inspection (manual or automated using computer control) (see FIG. 4).

The microfluidic chamber is then used for separation of sperm from epithelial cells, and HOT 100 can be used in another embodiment, for subsequently sorting the sample 302 placed in the input chamber 304 into individual chambers 305 (if desired). In particular, since sperm tend to stick to chamber or well 304 edges, it may be easy to increase throughput (i.e., how many sperm cells can be sorted in a given time), and also avoid interference from contaminating non-sperm cells if there are more than one output chamber/well 305 of the multiple connecting channels 306 emanating from the input chamber/well 304. This arrangement will improve reliability and efficacy in sperm sorting.

After sorting has been performed using microfluidic streaming or by using HOT 100, the chambers 305 can be sealed off from the input chamber 304 using conventional means, such as valves/stoppers. Alternatively backflow of sorted objects can be prevented by reducing (modulating) the dimension (typically width) of the channels rather than keeping them uniform throughout a given microfluidic chip.

Lysis of sperm in their individual chambers 304 is then performed on the microfluidics chip 300, and then the lysate can be extracted manually or using robotics, in order to extract the DNA. DNA from each sperm is then placed in a separate chamber 305 either on the same chip 300, or in an alternative embodiment, on a second chip, as described in the first embodiment.

As stated above in the first embodiment, the chip 300 with the extracted DNA is then placed on a PCR (thermocycler) machine 301 for amplification using STR primers. STR analysis is then run on the PCR amplified DNA (i.e., run gels to identify bands against standard STR markers).

Thus, single-cell PCR-based STR analysis can be performed in this embodiment as well.

Finally, as stated above, a final STR report is generated for individual sperm analyses and statistics are generated for appropriate matching against a standard database (e.g., CODIS for human identification).

Thus, as stated above, HOT 100 is used with PCR-based STR analysis, to allow single cell analysis and standard bulk (multi-cell) analysis. Further, as described above, HOT 100 allows individual cells to be moved, rotated and manipulated in three dimensions. One can use visible or infrared illumination for optical trapping to identify and move the sperm cells thereby separating them from contaminating epithelial cells in a sample. Use of visible or infrared excitation light eliminates major concerns of cell damage which may be encountered when using UV light. The sorted sperm cells can be introduced into a separate chamber each (i.e., one or a few cells of the same kind in a given chamber) and the desired PCR-based STR analysis in situ or otherwise, can be performed.

One can therefore, choose to carry out the subsequent PCR and STR analysis on single or multiple sperm cells offering all the advantages of single cell analysis as compared to standard bulk analysis.

As stated above, the PCR-based STR analysis can also be performed on-chip, so that only a single chip is used from start to finish.

In a third embodiment consistent with the present invention, the microfluidics chip 400 of the second embodiment is modified such that the rate of flow of the fluid from the input chamber 401 (see FIG. 5), the channel 403 dimensions (i.e., length, width, depth) and materials for the chip 400 itself, are controlled and the flow is adjusted in a manner such that no two cells from sample 402 occupy the same position inside the channel 403, or more critically, near junction 404, and therefore, single cells can be sorted through channels 405 into chambers 406-409, etc. One chamber (i.e., 406) contains ideally one cell.

Figure 5:
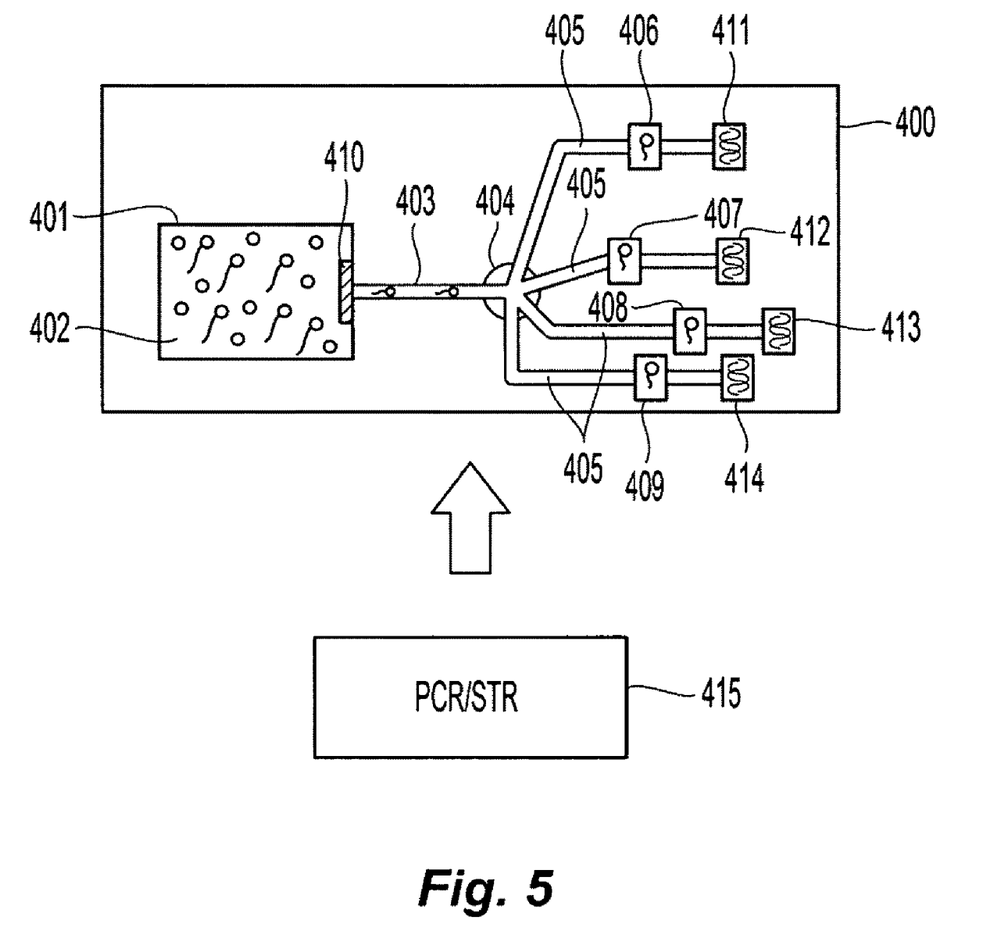
FIG. 5 is a schematic of an object sorting apparatus according to another embodiment consistent with the present invention, including a microfluidics chip, and a PCR/STR apparatus.

In addition, a filter 410 may be incorporated to only allow sperm cells to enter channel 403.

The cells can be lysed in chambers 406-409 and the corresponding chambers 411-414 will contain the extracted DNA from individual cells. DNA in chambers 411-414 can be PCR'ed 415 on-chip in one embodiment (as described above), or can be transferred to another chip either via pipetting or through active (pumping) mechanisms, or even using robotic arms to carry out the DNA transfer.

In an alternative embodiment, the input chamber 401 containing the sample 402 (cell mixture) eluted from the swab can be constructed in a layered format where sperm cells can be allowed to settle on the bottom of the chamber 401 and can be constructed as emanating from that layer, to draw individual cells through channel 403. The layers contain separate sets of channels and do not allow cell admixture. Valves may be incorporated in the microfluidic chips 400 to prevent backflow of sorted materials.

In a fourth embodiment consistent with the present invention, eluted cells from a sample 500 (see FIG. 6)—are eluted into an inlet chamber 501 on a microfluidic chip 502, where the sample 500 is deposited.

Figure 6:
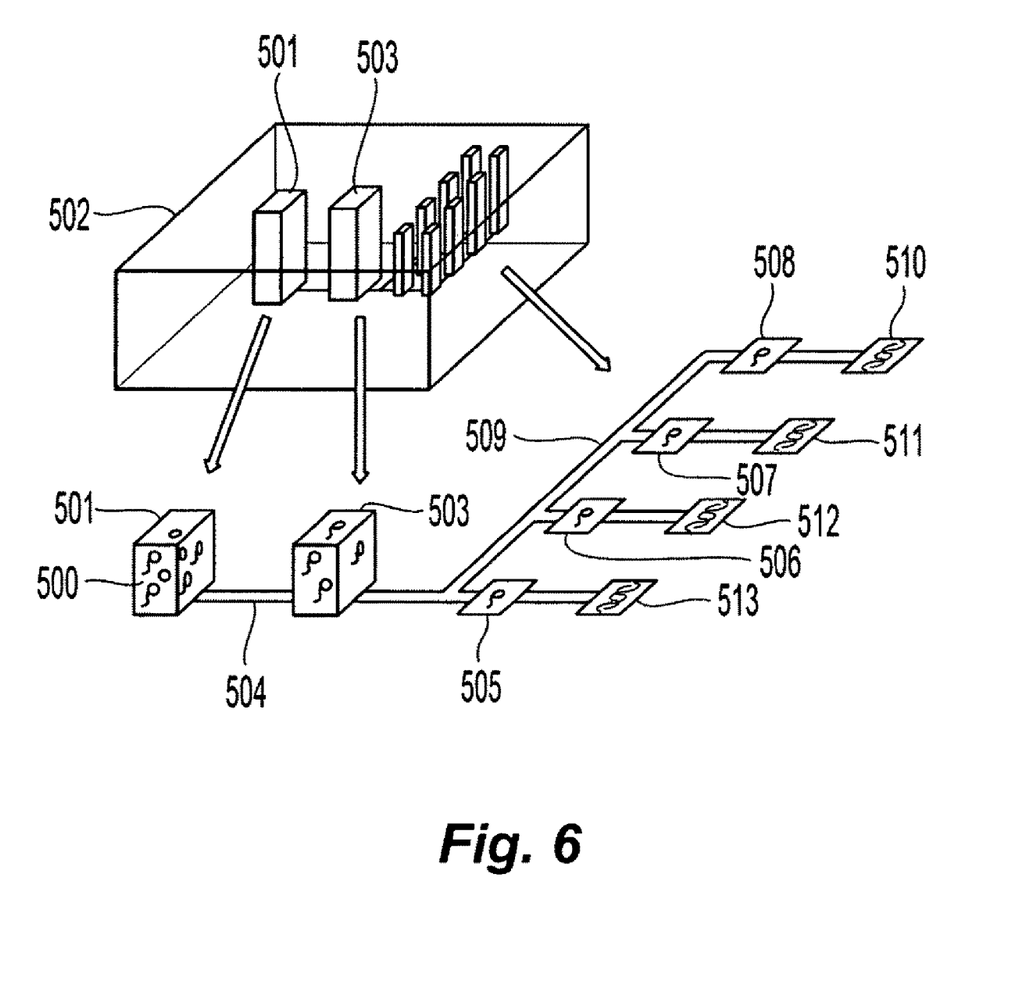
FIG. 6 is a schematic of an object sorting apparatus according to another embodiment consistent with the present invention, including a microfluidics chip and an on-chip PCR/STR apparatus.

Contaminants (i.e., epithelial cells) from the sample 500 settle on the bottom of the inlet chamber/reservoir 501 and sperm cells are mobilized via fluid flow through channel 504 to collect in outlet chamber reservoir 503. In a second stage, individual collection reservoirs 505-508 collect sperm sorted via channel 509, according to previously described methods.

In a third stage, lysis of individual sperm takes place in chambers 510-513, with the extraction of the DNA being accomplished by single cell PCR (on-chip PCR) according to previously described methods.

In another embodiment, the process of the PCR and STR analysis can be automated and high speeds can be achieved which will eliminate another bottleneck often experienced in the current approaches used in STR analysis. Currently differential extraction is almost entirely manually operated. Other techniques like mechanical sorting using mesh filters of varying pore sizes (trak-etch filtration) are also not conducive to automation which tends to clog the filters. However, HOT-based sorting of sperm from epithelial cells can be easily automated. Automation will cut down on operation costs and time and thereby solve more sexual assault cases in a given time.

In yet another embodiment consistent with the present invention, the methods proposed are compatible with automation and multiplexing—i.e., running multiple forensic sample analyses, thereby increasing throughput.

In yet another embodiment consistent with the present invention, coupling with robotics where multiple crime samples can be eluted, separated and tested at the same time, thereby increasing throughput, includes additional advantages since it is platform independent—i.e., can be carried out on glass slides (glass coverslips) or in test tubes or in Eppendorfs or even in 96-well format (given that there are machines now that can do PCR in 96-well or higher-well formats, in situ PCR is possible using such separation). Robotic handling avoids other source of contamination which could arise from operator handling of the cell samples.

As stated above, this methodology is also compatible with in situ PCR on forensic samples. Therefore, all advantages of in situ PCR will be valid such as to:

(i) reduce chance of contamination since in situ PCR will involve fewer steps and avoid transfer of samples from one container to another; and (ii) cut down cost of such forensic analysis by limiting supply cost that is likely involved with more steps and transfer of samples.

Thus, due to limited DNA content from a single cell, the number of PCR cycles before STR analysis will be increased as compared to existing multi-cell (bulk) PCR based methods.

To approach the issue of equal amplification of the 13 STR fragments using genomic DNA as template amplicon from a single sperm, one can run real time PCR as a control for additional quality control without compromising time or efficiency. Also, multiplex PGR can be performed in the same way on a single cell as is done with multiple cells.

Thus, single cell PCR based forensics offers additional advantages for analyzing crime samples without compromising what existing bulk (multiple cell) PCR based forensics offers.

Finally, as stated above, single cell PCR can be automated and can also be performed on chip (on-chip PCR) furthering opportunities for miniaturization and portability.

The opportunity for miniaturization and portability opens the scope of single cell PCR based forensic DNA analysis beyond sexual assault crime cases to human identification of war victims or war soldiers (in the realm of military forensics, for example), and even paternity testing where, often, collection of enough sample(s) from the suspect is a problem.

The virtue of individual sperm STR readout is that it increases the likelihood of detecting multiple assailants (if involved in a sexual assault case) based on the statistical significance of the STR readout (well-established by standard regulations). It also enhances the chance of ruling out incriminated persons in a sexual assault case where limited samples (<200 sperms could be obtained) were available for analysis. In rare cases, where allele dropout is a problem and an STR profile (based on standard bulk PCR analysis) could not be matched to CODIS database (the dominant allele masking the other), there is a greater likelihood of matching an STR signature as obtained from single cell PCR to the database with relevant statistical calculations, to arrive at the needed probability. Thus, the present invention is advantageous in resolving many problems now existing in forensics DNA analysis.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A method of sorting objects and identifying the objects in a sample, comprising:

providing a holographic optical trapping apparatus;

providing a sample, said sample containing objects to be separated, in a fluidic stream in a microfluidics chip having an input chamber and a plurality of output chambers;

streaming said sample from said input chamber and through said microfluidics chip into said plurality of output chambers;

optically trapping said objects in said sample at said input chamber, using said holographic optical trapping apparatus;

sorting said optically trapped objects into wanted and unwanted objects;

individually removing said wanted objects into each of said plurality of output chambers such that each of said output chambers contains a single wanted object; and performing single-cell PCR-based STR analysis downstream from said plurality of output chambers on each of said single wanted objects to determine an identification of each of said single wanted objects.

2. The method according to claim 1, wherein said sorting step, said performing step, and said PCR/STR analysis step, are performed on a single microfluidics chip.

3. The method according to claim 1, wherein the wanted objects are cells and the unwanted objects are contaminants.

4. The method according to claim 1, wherein the wanted objects are cancer cells and the unwanted objects are healthy cells, or vice versa.

5. The method according to claim 1, further comprising: providing a filter at an outlet of said input chamber.

6. The method according to claim 5, further comprising: providing valves at said input chamber to prevent backflow.

7. The method according to claim 1, wherein said sorting and PCR performing steps are automated and multiplexed.

8. A method of sorting objects and identifying the objects in a sample, comprising:

providing a microfluidics chip having an input chamber and a plurality of output chambers;

providing a sample in a fluidic stream in said input chamber, said sample containing objects to be sorted;

streaming said sample from said input chamber and through said microfluidics chip into said plurality of output chambers;

sorting said objects using said microfluidics fluid stream, such that said objects are sorted into wanted and unwanted objects;

individually removing said wanted objects into each of said plurality of output, chambers, such that each of said output chambers contains a single wanted object; and performing single-cell PCR-based STR analysis downstream from said plurality of output chambers on each of said single wanted objects to determine an identification of each of said wanted objects.

9. The method according to claim 8, wherein said sorting step, said performing step, and said PCR-based SIR analysis step, are performed on a single microfluidics chip.

10. The method according to claim 8, wherein the wanted objects are cells and the unwanted objects are contaminants.

11. The method according to claim 8, wherein the wanted objects are normal cells and the unwanted objects are cancerous cells, or vice versa.

12. The method according to claim 8, further comprising: providing a filter at an outlet of said input chamber.

13. The method according to claim 12, further comprising: providing valves at said input chamber to prevent backflow.

14. The method according to claim 8, wherein said sorting and PCR performing steps are automated and multiplexed.

15. The method according to claim 1, wherein said wanted objects are sperm cells.

16. The method according to claim 8, wherein said wanted objects are sperm cells.

17. The method according to claim 1, further comprising: controlling the streaming of said sample such that no two objects from said sample occupy a same position in a channel or at a junction in said microfluidics chip.

18. The method according to claim 1, wherein said unwanted objects settle in said input chamber, and said wanted objects flow into said plurality of output chambers.

19. The method according to claim 1, wherein said wanted objects are streamed into a single output chamber prior to being streamed into said plurality of output chambers.

20. The method according to claim 1, wherein each of said single wanted objects flows from each of said individual output chambers to a corresponding individual lysis chamber where said PCR-based STR analysis is performed on each of said single wanted objects.

21. The method according to claim 8, further comprising: controlling the streaming of said sample such that no two objects from said sample occupy a same position in a channel or at a junction in said microfluidics chip.

22. The method according to claim 8, wherein said wanted objects are streamed into a single output chamber prior to being streamed into said individual output chambers.

23. The method according to claim 8, wherein said unwanted objects settle in said input chamber, and said wanted objects flow into said plurality of output chambers.

24. The method according to claim 8, wherein each of said single wanted objects flows from each of said individual output chambers to a corresponding individual lysis chamber where said PCR-based STR analysis is performed on each of said single wanted objects.

25. The method according to claim 8, further comprising:
a holographic optical trapping apparatus which optically traps and sorts said wanted objects from said unwanted objects at said input chamber.

26. The method according to claim 25, wherein said microfluidics chip is optically transparent.

27. The method according to claim 1, wherein said microfluidics chip is optically transparent.

* * * * *